United States Patent [19]
Balfanz et al.

[11] Patent Number: 5,493,923
[45] Date of Patent: Feb. 27, 1996

[54] PROCESS AND DEVICE FOR TAKING SAMPLES FROM WASTE GASES

[75] Inventors: Eckhard Balfanz, Muenster; Werner Funke, Havixbeck; Johann König, Muenster; Jochen Theisen, Havixbeck; Heinz Linnemann, Muenster, all of Germany

[73] Assignee: GFA Gesellschaft zur Arbeitsplatz-und Umweltanalytik mbH, Muenster, Germany

[21] Appl. No.: 140,103

[22] PCT Filed: Feb. 25, 1993

[86] PCT No.: PCT/EP93/00434

§ 371 Date: May 27, 1994

§ 102(e) Date: May 27, 1994

[87] PCT Pub. No.: WO93/17331

PCT Pub. Date: Sep. 2, 1993

[30] Foreign Application Priority Data

Feb. 26, 1992 [DE] Germany ............ 42 05 792.2

[51] Int. Cl.⁶ ...................................... G01N 1/24
[52] U.S. Cl. .................. 73/863.21; 73/863.12; 73/863.25; 73/864.34
[58] Field of Search ............ 73/863.21, 863.22, 73/863.12, 863.23, 863.24, 863.25, 863.83, 863.84, 864.34, 864.73, 23.31, 23.32, 23.33, 28.01, 28.04, 28.05, 28.06, 31.02, 31.03, 863.31

[56] References Cited

U.S. PATENT DOCUMENTS

| | | | |
|---|---|---|---|
| 3,759,087 | 9/1973 | Iwao et al. ................ | 73/863.12 |
| 3,903,745 | 9/1975 | Bolser ....................... | 73/863.21 |
| 3,933,431 | 1/1976 | Trujillo et al. ............ | 73/836.21 X |
| 4,034,611 | 7/1977 | Horling ...................... | 73/863.12 |
| 4,191,541 | 3/1980 | Jenkins ...................... | 73/863.12 |
| 4,470,316 | 9/1984 | Jiskoot ...................... | 73/863.31 X |
| 4,630,464 | 12/1986 | Maul et al. ................ | 73/23.33 |
| 4,686,848 | 8/1987 | Casselberry et al. ...... | 73/863.12 X |
| 4,759,210 | 7/1988 | Wohltjen . | |
| 4,883,505 | 11/1989 | Lucero ....................... | 73/863.21 X |
| 5,058,440 | 10/1991 | Groze, Jr. .................. | 73/863.83 |

FOREIGN PATENT DOCUMENTS

| | | |
|---|---|---|
| 164591 | 12/1987 | European Pat. Off. . |
| 9004227 | 7/1990 | Germany . |

OTHER PUBLICATIONS

Extract from German Chemical Dictionary *Romps Chemie–Lexikon*, 1 page showing most of a Definition of Amberlite® in German, published 1979.

Pp. 57–63, 70, 71, 73, and 74 of a Prospectors of Merck Laborprodukte published by Sep. 1995 in German.

*Patent Abstracts of Japan*, Abstract Published Nov. 13, 1981

(List continued on next page.)

*Primary Examiner*—Thomas P. Noland
*Attorney, Agent, or Firm*—Karl F. Milde, Jr.

[57] ABSTRACT

The invention concerns a process and a device for taking samples in particular from waste gases containing substances of moderate and low volatility in a gas or aerosol phase. To this end, a partial current is diverted and conducted into a separation area (10), where the substances to be tested from the partial current, either in dust-bonding form or in the condensate, undergo a separation process and are fixed. When applied to a specific sample for the analysis of organic substances of medium to low volatility, in particular polychlorinated dibenzo(p)dioxins (PCDD) and polychlorinated dibenzofurans (PCDF), the separation process can be restricted according to the invention in such a way that the partial current, together with the gaseous and liquid water portion contained in it, undergoes a two-stage separation process, where it is drawn through an inert dust-filter region (11), and drawn through a region (12) filled with an adsorber such as a synthetic adsorbent resin with a multi-reticular structure. The gaseous water contained in the waste gas is not removed before being drawn into the adsorber region, nor is the dew point lowered by dilution.

12 Claims, 1 Drawing Sheet

OTHER PUBLICATIONS vol. 5113, Group P089 (56–108954) "Analytical Method of Moisture".

*International Laboratory* Bd. 14, No. 1, pp. 10, 12–14, 16, 18, 20, 22, 23 Jan.–Feb. 1984, Gregory A. Junk et al., "Sampling Methods for Organic Compounds in Stocks".

*Analytical Chemistry,* Bd. 57, No. 6, May 1985, pp. 1138–1144, Mary P. Ligocki et al. "Assessment of Adsorption/Solvent Extraction with Polyurethane Foam and Adsorption/Thermal Desorption with Tenax/GC for the Collection and Analysis of Ambient Organic Vapors".

*Patent Abstracts of Japan,* Grp. P1254, vol. 15, No. 372, Abs Pub date Sep. 19 1991 (3–146861) "Method for Measuring Fluorocarbon".

PROCESS AND DEVICE FOR TAKING SAMPLES FROM WASTE GASES

BACKGROUND OF THE INVENTION

The invention concerns a method of sampling waste gas emissions, especially those containing substances of moderate to low volatility suspended in a gas or aerosol.
The method comprises two steps:

(a) In the first step some of the emissions are withdrawn from the outlet, cooled if necessary, and forwarded to a separator. The substances to be identified, as gases either attached to particles of dust or in a condensate, are subjected to a separation and fixed.

(b) In the second step the substances are extracted and introduced into an analyzer.

Methods of this nature are described in drafts of VDI Guideline 3499, Sheets 1–4: "Messen von polychlorierten Dibenzo(p)dioxinen (PCDD) und Dibenzofuranen (PCDF) in Abgasen industrieller Anlagen und Feuerungsanlagen". This Guideline prescribes how to measure the polychlorinated dibenzo(p)dioxins (PCDD's) and dibenzofurans (PCDF's) in emissions from industrial plants and furnaces.

PCDD's and PCDF's are classes of related chlorinated aromatics. The first comprises 75 and the second 135 homologs. The aforesaid VDI Guideline lists all the isomers and illustrates their structures.

PCDD's and PCDF's derive from the heating or burning of chlorinated organic materials and as undesirable by-products in the manufacture or processing of organochlorine chemicals. They are relatively stable substances that can, however, be broken down in furnaces at high temperatures. The occurrence and chemistry of PCDD's and PCDF's and their toxicologies and ecological hazards have been thoroughly described (cf. the bibliography in the aforecited Guideline).

The Guideline describes standard methods of determining contents of PCDD's and PCDF's. The procedure is intended for the analysis of emissions from a very wide range of sources. Raw, pure, and synthesis gases from internal-combustion engines, domestic furnaces, cement plants, fluidized beds, shredders, landfills, ceramics, metals, and organic- and inorganic-chemicals plants, smelters for specialty recycling, sludge-burning plants, lignite- and anthracite-stoked furnaces, wood-burning plants, oil- and gas-fueled plants, garbage incinerators, and pyrolysis plants are to be analyzed.

The analyzed-gas temperatures can range from −30° to more than 1000° C. The waste gas emissions contain very different levels of water. Dust concentrations can be more than 1 g/m$^3$, in a raw gas upstream of an electric filter for example.

The procedure described in the VDI Guideline is complicated. The emissions to be analyzed are pumped through a particle filter in the form of a cylinder packed with quartz wool. The filtered gas is forwarded to a condensate separator, where it is cooled to 3° to 20° C. Downstream of the separator is a cartridge packed with a solids adsorbent. Every surface that the sample can come into contact with is glass, with the exception of elbows and part of the filter head, which are titanium. The exhaust pipe can be air-cooled when the emission is hotter than 120° C. The temperatures in the particle filter accordingly range between 80° and 100° C. or even substantially lower.

Every surface that the sample has come into contact with must be washed with recirculating acetone or toluene subsequent to every procedure. The glass liner of the exhaust pipe is generally divided into 10-cm long sections.

The vehicles analyzed are the glass exhaust-pipe liner, the dust-laden quartz wool, the condensate, the solids adsorbent, and the used acetone or toluene rinse.

The result is five subsidiary samples, each of which must be extracted, shaken out, or redissolved. The resulting solutions must then be purified and combined for further processing prior to the actual analysis.

A lot of the moisture in the emissions is removed prior to introduction into the inert filter (sheets 1 & 2), the adsorber (sheets 1, 2 & 4), or the absorber (sheet 3). The moisture is condensed (sheets 2–4) or diluted (sheet 1) out. Dilution entails heating the exhaust pipe to prevent material from condensing onto and possibly adsorbing into its inner surface, leading to erroneous results.

With the known procedure, for due attention to be devoted to all substances of interest, it is necessary to provide either complicated devices that will completely filter the waste gas emissions at low temperatures (sheet 1) or interception of the concentrate somewhere upstream of the last precipitation (adsorption or absorption) to prepare it separately for analysis.

Known apparatus described on sheet 2 of the aforesaid VDI Guideline 3499 essentially comprises a dust filter, a condensate separator, an adsorber, and a suction pump with a flowmeter.

The separator comprises a 2-liter three-neck flask with a cock and two standard-ground joints. Each outer joint accommodates a rapid cooler. The sample flows down through the one cooler (a commercially available high-intensity condenser), through a condensate collector accommodated in a 2-liter mushroom-hooded heater, and through the other cooler (with a radiating area of 3000 cm$^2$). The droplets precipitate in a downstream glass cylinder packed with Rashig rings. The gas arrives next in a glass cartridge packed with 250 ml of adsorbent resin.

This apparatus is extremely difficult to manage and demands highly trained personnel. Rinsing with and processing the inflammable acetone and toluene and preventing them from escaping into the atmosphere demands extreme caution. The subsequent purification is also very complicated and takes at least an hour.

SUMMARY OF THE INVENTION

One object of the present invention is accordingly to provide a method of sampling for the analysis of PCDD's and PCDF's which will permit as much sensitivity as known methods while being essentially simpler and more efficient. The method in accordance with the invention requires neither concentration nor dilution for the analysis.

This object is attained in accordance with the present invention in a method of the type initially described. The method differs from the prior art in that the withdrawn waste gas emissions destined for analysis, containing substances of moderate to low volatility, particularly polychlorinated dibenzo(p)dioxins (PCDD's) and dibenzofurans (PCDF's), are separated in two steps: (1) passing the emissions through an inert dust filter, and (2) passing them through an absorber (e.g. a synthetic-resin adsorbent with a multireticulate structure). The organic substances that adhere to the filter and adsorbent are then analyzed.

The method is basically applicable for sampling emissions containing organic substances which are gaseous or are attached to dust and suspended in a gas or aerosol, furnace-flue gases for example. Tests indicate that the method is especially appropriate for sampling such polyhalogenated aromatics as polychlorinated benzenes, phenols, biphenyls, dibenzo(p)dioxins, and dibenzofurans, polybrominated dibenzo(p)dioxins and dibenzofurans, polybrominated and polychlorinated dibenzo(p)dioxins and dibenzofurans, and polycyclic aromatic hydrocarbons.

The method and apparatus in accordance with the present invention will be specified hereinafter with polychlorinated dibenzo(p)dioxins (PCDD's) and polychlorinated dibenzofurans (PCDF's) as examples.

Another object of the present invention is to provide apparatus for carrying out the method. This object is attained in accordance with the invention in apparatus of the type decribed above with the features that will now be described. The apparatus has a heat-resistant probe with an intake into a gas line that can be cooled if necessary. A cartridge can be attached downstream of the gas line. The cartridge is in two sections and has an outlet. The upstream section is packed with an inert and insoluble filter material, quartz wool for instance. The downstream section is packed with an adsorbent, a multireticulate resin for instance. A line with a section pump at the other end is attached to the outlet.

The method and apparatus in accordance with the present invention differ from those known in the art, which also employ an adsorbent, in that the adsorbent adsorbs every constituent that contains PCDD's and PCDF's and does so without complicated prior cooling and/or condensation-point reduction for the purpose of collecting a concentrate. It has been observed that the adsorbent is highly effective when moist or liquid, and tests have indicated that it completely adsorbs the PCDD's and PCDF's.

Since more than 99% of the dioxins and furans are adsorbed and fixed in the cartridge's two sections, subsequent analysis can be confined to their contents. Since the two sections are individually made of glass, they are also easy to clean or dispose of.

Such known insoluble synthetic polystyrene polymers and acrylates as Amberlite XAD-2, Amberlite XAD-4, Amberlite XAD-7, and Amberlite XAD-8 have been proven effective as adsorbents. These products are manufactured by E. Merck of Darmstadt, Germany. Amberlite XAD-2 has in particular turned out to be cost-effective and easy to handle.

The filter is preferably packed tight with quartz wool, glass fibers, glass felt, or other dust-intercepting vehicles.

One embodiment of the invention will now be specified by way of example with reference to the drawing.

BRIEF DESCRIPTION OF THE DRAWING

The sole FIGURE is a schematic side view of sampling apparatus.

DESCRIPTION OF THE PREFERRED EMBODIMENTS

Figure 1:
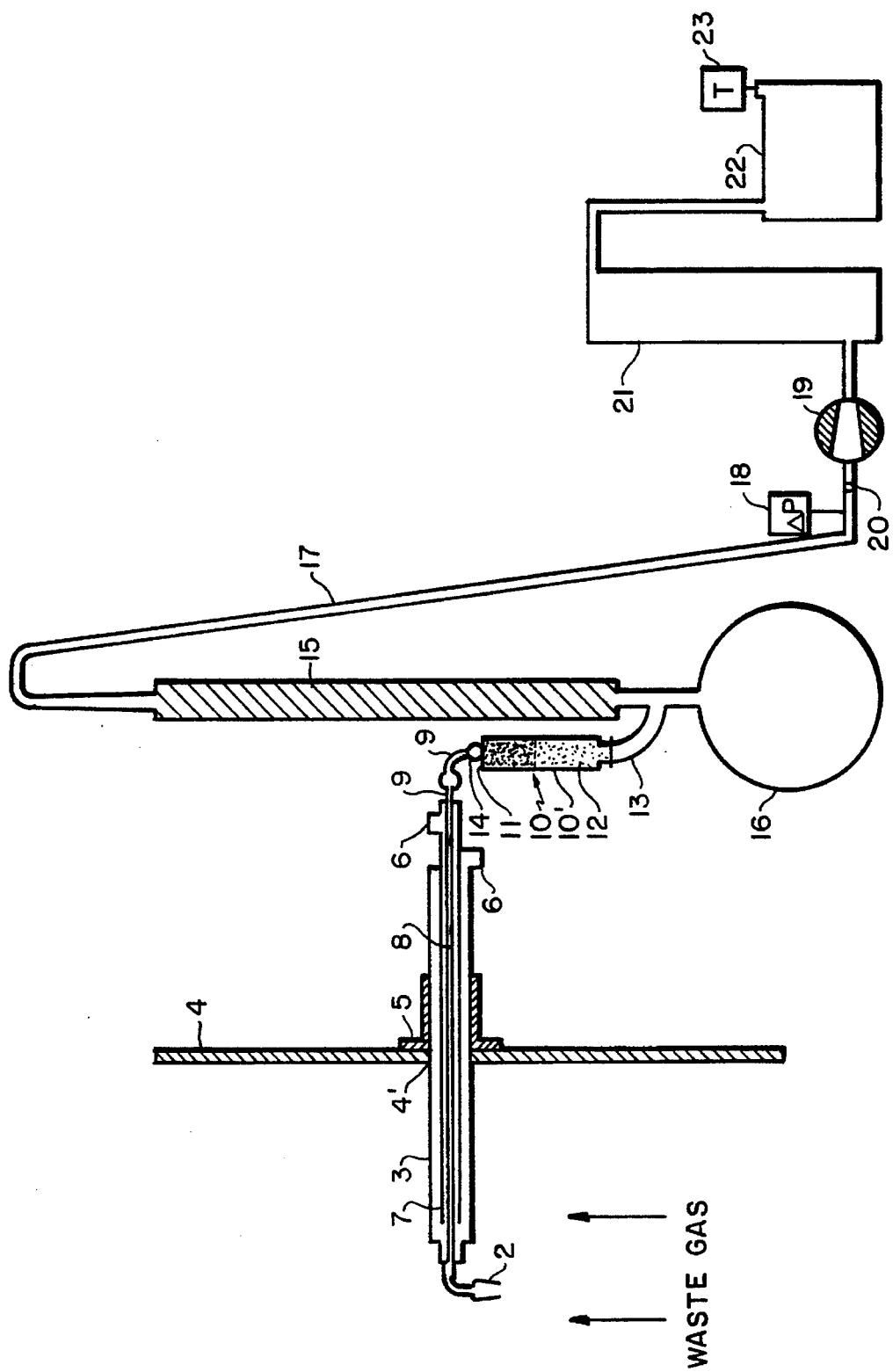

Emissions from a garbage incinerator, for example, travel through an emissions outlet 1 in the direction indicated by the arrows. There is an aperture 4' in the wall 4 of outlet 1. Aperture 4' is surrounded by a flanged probe guide 5. The aperture can if necessary be sealed by an unillustrated diaphragm. A tubular probe 3 is inserted through a probe guide 5 and aperture 4'. The probe 3 can be specifically designed for the particular assignment, type of gas being analyzed, and sampling point. It can be made of glass, quartz, PTFE, titanium, or steel. It will generally be made of extra-strong glass (Duran) or quartz glass. Probes of this kind are known. If its detecting cross-section, length, and resistance to mechanical stress so dictate, the probe can also be protected by a cylindrical jacket. If the sampling is to occur isokinetically, the probe should be provided with an intake 2 that projects out and bends as specified in VDI Guideline 2066. The same Guideline is to be consulted in designing the probe's cross-section.

Extraordinarily high concentrations of dust in the gas being analyzed may require an upstream separator, a cyclone and filter packed with quartz wool for example. This component is not illustrated herein.

If necessary, the gas can be cooled to condition it. Probe 3 is for this purpose provided with a jacket 7 to cool it with water supplied through an inlet-and-outlet 6. Inside the tubular probe 3 is a glass liner 8 that extends back from an intake 2, through the cooling jacket 7, to the end of the probe outside the outlet 1, and into a transitional elbow 9, which is not essential to the invention and can be eliminated from some designs. An opening-and-closing valve 14 can, if necessary, be inserted between this point and the downstream components. The liner is as short and smooth as possible to prevent deposits on its inner surface.

The gas withdrawn through the probe, through its liner that is, can contain aggregated or embedded solid, liquid, or gaseous organic constituents. The solids can be in the form of, or attached to, particles. The liquid can consist of droplets. The constituents can be dissolved, suspended, or dispersed in the condensate.

The sample, loaded with the aforesaid constituents, travels through the elbow 9, if any, and into a preferably glass cartridge 10. Cartridge 10 can be divided by a preferably perforated glass partition 10' into two sections 11 and 12. Upstream section 11 accommodates a filter, tightly packed quartz wool in the present embodiment, that traps dust.

Although cartridge 10 is in the form of an elongated glass tube by way of example in the present embodiment, it could also be spherical, hexahedral, etc. and made of a material, titanium for example, other than glass. Instead of quartz wool, the upstream section 11 could also be packed with glass fibers or other materials that are insoluble and will not react with the precipitating substances.

The downstream section 12 of cartridge 10 is packed with an adsorbent in the form of a synthetic resin with a multireticulate structure. Appropriate, by way of example, are the various porous polymers commercially available under the brand names Amberlite XAD, Carbopak-C, and Tenax-GC from various manufacturers. Not to be excluded, however, are expanded polyurethanes, silica gel, or other adsorbents that have the ability to quantitatively adsorb and desorb organic constituents without modifying them.

Among the factors to be considered in selecting and positioning the filtering and adsorbing materials are to what extent they will impede the flow of the gas and to what extent their adsorbency depends on temperature. The adsorbency of a material can be increased by cooling it. If capacity is limited, sampling time can be extended by replacing the filter-and-adsorber cartridge. This can be done manually or through the timed diversion to other identical cartridges by multiple-way valves known in the technology of adsorption.

Packing each 100 $cm^3$ of the upstream section tight with 10 to 15 g of quartz wool has been demonstrated to be ideal. The downstream section is preferably entirely packed with the adsorbent Amberlite XAD-2, manufactured by E. Merck of Darmstadt, Germany. The temperature of the gas traveling through the cartridge is between 25° and 150° C. At the downstream end of the cartridge is an outlet 13. Outlet 13 opens into the base of a condenser 15.

The filtered gas flows through the condenser 15. Condensate and water collects in a bulb 16. The clean gas flows through a line 17, possibly accommodating an opening-and-closing valve 20, to a pump 19.

Drying can be augmented by removing any residual moisture with a desiccant, silica gel for instance, in a drying column 21. The capacities of the condenser and drying column will depend on the expected properties, including temperature and moisture, of the gas being sampled.

Lines forwarding 0.1 to 10 m$^3$/hour, depending on prevailing conditions (total volume and rate of flow in accordance with the requisite sensitivity of analysis, the nature of the gas, and the limiting conditions of the assignment, e.g. its isokinetics) can ordinarily be employed.

The gas-forwarding system can include a diaphragm-based vacuum pump, dry-running or oil-vacuum rotating-disk pumps, ejector pumps, and branch-channel fans.

The rate of flow can be regulated by a valve 20 in accordance with results from a pressure gauge 18.

The valve can alternatively be controlled at the suction intake into a pump 19 in accordance with a prescribed flow rate, with the instant rate obtained by measuring the pressure difference at a diaphragm, hot-wire anemometer, electromagnetic-contact flowmeter, etc. The rate of flow can also be regulated by computer, with the parameter in the form of the dependence of the varying instantaneous pressure in the line being detected by an appropriate anemometer or Pitot tube.

The volume of emission withdrawn is determined in relation to air pressure and temperature at a gas meter 22 combined with a thermometer 23. The instruments are of known types and are also employed at state of the art. Components 13 through 23 are in fact all of known types and can be modified in accordance with the particular analysis assigned.

Depending upon the circumstances, the pressure, water content and temperature of the gas is prescribed in accordance with its volume. These parameters are very frequently 1013 hPa, 0° C., and dry. The volume will usually have to be readjusted by drying the gas and establishing temperature and pressure simultaneously against the volume-detection instrumentation.

Assembling and testing the apparatus will now be specified.

A clean liner 8 is inserted in probe 3. It must be 100% air tight to prevent the atmosphere from contaminating the results. The packing can, depending on the temperature of the sample, comprise strands of mineral fiber or Teflon. Resilient gaskets and shaft seals can also be employed.

The probe 3 is inserted into the outlet 1 through the guide 5. An opening-and-closing valve 14, positioned as adjacent as possible to liner 8, is initially closed. Once the apparatus has been assembled, its tightness is verified at a vacuum of 500 mbars, which must not increase over the interval of a minute.

Sampling follows, with flow rate and temperature measured at regular intervals along the volume-regulating system.

When sampling is concluded, the pump 19 is turned off and the valve 14 closed. The volumes of waste gases withdrawn are recorded. Any condensate in bulb 16 can be pumped out and disposed of.

Cartridge 10 is removed from the system and the glass sealed and protected from light. The filtering material and adsorbent are processed by known methods, usually extraction, decomposition, purification, gas-chromatography, in the laboratory. Tests have revealed practically no significant levels of adsorbate left in the rest of the apparatus in relation to the PCDD's and PCDF's being analyzed.

The apparatus can accordingly be used again immediately as soon as a new cartridge has been inserted and the liner 8 replaced. Although the cartridge will always contain some moisture since its temperature is maintained below the condensation point, this situation will have a positive rather than a negative effect on the results because the gas, flowing for several hours, will produce a residual-moisture equilibrium in the adsorbent in the cartridge.

The dust filter can be eliminated if the level of dust that the volatile substances can attach to during the filtering process is negligible or low. The probe can also be eliminated if the sampling point is appropriately designed. It is also possible to position the cartridge upstream and the pumps downstream of the probe.

The method and apparatus in accordance with the present invention have many advantages, some of which will now be described.

The method is almost independent of the temperature (0°–1000° C.), moisture (as much as 300 g/m$^3$ or more), and dustiness (as much as 1 g/m$^3$) of the waste gas emissions.

It is unnecessary to dilute the gas to lower its condensation point or to collect the precipitated condensate for analysis.

The expenditure is comparable to that of dust detection. Less time is spent on site, making the sampling more economical. Analysis is also more economical in that the extracts have to be obtained from one, or at most two collected phases.

Replacing the probe liner and cartridge with its dust filter and adsorbent resin in preparation for subsequent sampling takes only a few minutes. It is unnecessary to clean the apparatus on site with combustible solvents for example.

Since the only surfaces of the apparatus contacted by the sample are the inner surfaces of the liner and cartridge, the potential for secondary contamination and blanks from the apparatus is minimized.

The apparatus is easy to handle. Instead of as many as five vehicles (liner, filter, condensate, adsorbent, and rinse) that need to be analyzed at state of the art, the present invention necessitates only one (the cartridge with its filter and adsorbent) or possibly two (the cartridge and the probe liner).

Since the cartridge with its filter and adsorbent can be spiked with $^{13}$C-PCDF/D standards at the laboratory ahead of time, there is no need to spike the apparatus on site.

The probe apparatus according to the invention is much less expensive than the known apparatus.

Another particular advantage of the method is that it can be carried out continuously and permanently. Constant monitoring accordingly becomes possible. Cartridges can be installed in parallel branches and alternately operating, always with one on line and the other or others being replaced or on standby.

There has thus been shown and described a novel process and device for taking samples from waste gases which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In a method of sampling waste gas emissions which contain substances selected from the group consisting of polychlorinated dibenzo(p)dioxins (PCDD's) and dibenzofurans (PCDF's) suspended in a gas or aerosol, said method comprising the steps of:

(a) obtaining a sample of said waste gas emissions from a waste gas stream;

(b) separating and fixing said substances from the sample, either in dust-bonded form or in a condensate; and (c) analyzing said substances to identify their constituents;

the improvement wherein said separating step comprises the steps of:

(1) passing said sample through an inert dust filter; and (2) thereafter passing said sample through a synthetic-resin absorbent selected from the group consisting of (i) a copolymer of styrene and divinylbenzene and (ii) an acrylate, whereby organic substances that adhere to the filter and the adsorbent are then analyzed.

2. The method defined in claim 1, further comprising the step of cooling said sample before it is passed through said filter.

3. The method defined in claim 2, wherein said sample is cooled to below 200° C.

4. The method defined in claim 1, wherein said synthetic-resin adsorbent is selected from the group consisting of Amberlite® XAD-2 and Amberlite® XAD-4.

5. The method defined in claim 1, wherein said synthetic-resin adsorbent is selected from the group consisting of Amberlite® XAD-7 and Amberlite® XAD-8.

6. Apparatus for sampling waste gas emissions which contain substances selected from the group consisting of polychlorinated dibenzo(p)dioxins (PCDD's) and dibenzofurans (PCDF's) suspended in a gas or aerosol, said apparatus comprising, in combination:

(a) a heat resistant probe having an inlet for receiving a waste gas emissions sample from a waste gas stream;

(b) a separator for separating and fixing said substances from the sample, said separator including a separator cartridge having a first section connected to receive said sample from said probe and a second section connected to receive said sample from said first section and having an outlet, said first section having an inert and insoluble dust filtering material and said second section having a synthetic-resin adsorbent selected from the group consisting of (i) a copolymer of styrene and divinylbenzene and (ii) an acrylate; and (c) a suction pump connected to said outlet.

7. The apparatus defined in claim 6, wherein said probe includes a liner and means for cooling said liner.

8. The apparatus defined in claim 6, wherein said probe is integrated with said separator.

9. The apparatus defined in claim 6, wherein said synthetic-resin adsorbent is selected from the group consisting of Amberlite® XAD-2 and Amberlite® XAD-4.

10. The apparatus defined in claim 6, wherein said synthetic-resin adsorbent is selected from the group consisting of Amberlite® XAD-7 and Amberlite® XAD-8.

11. The apparatus defined in claim 6, wherein said first section is filled with a filter material selected from the group consisting of quartz wool, glass fibers, glass felt and membranes.

12. The apparatus defined in claim 6, wherein said separator comprises at least two separator cartridges connected to said probe in parallel, and means for operating said cartridges alternately, with one cartridge always on line while the other cartridges are being replaced or are on standby.

* * * * *